(12) United States Patent
MacDonald

(10) Patent No.: US 10,426,651 B2
(45) Date of Patent: Oct. 1, 2019

(54) NASAL INSERTS

(71) Applicant: SANOSTEC CORP, Beverly Farms, MA (US)

(72) Inventor: Louise S. MacDonald, Beverly, MA (US)

(73) Assignee: Sanostec Corporation, Beverly Farms, MA (US)

( * ) Notice: Subject to any disclaimer, the term of this patent is extended or adjusted under 35 U.S.C. 154(b) by 0 days.

(21) Appl. No.: 15/005,389

(22) Filed: Jan. 25, 2016

(65) Prior Publication Data

US 2016/0206468 A1 Jul. 21, 2016

Related U.S. Application Data

(63) Continuation of application No. 12/245,430, filed on Oct. 3, 2008, now Pat. No. 9,242,080.

(60) Provisional application No. 60/977,209, filed on Oct. 3, 2007.

(51) Int. Cl.
*A61M 29/00* (2006.01)
*A61F 5/08* (2006.01)
*A61M 16/00* (2006.01)

(52) U.S. Cl.
CPC .............. *A61F 5/08* (2013.01); *A61M 16/00* (2013.01); *A61M 29/00* (2013.01)

(58) Field of Classification Search
CPC .......... A61F 5/08; A61M 16/00; A61M 29/00
USPC ......... 128/830–833, 206.11, 230.18, 203.22, 128/207.18, 843; 623/1.1–1.15, 1.3–1.31, 623/1.22, 23.69, 23.7; 606/199, 213, 198, 606/191, 200; 434/279; 604/94.01
See application file for complete search history.

(56) References Cited

U.S. PATENT DOCUMENTS

| | | | |
|---|---|---|---|
| 682,123 | A | 9/1901 | William |
| 753,133 | A | 2/1904 | Gamble |
| 810,617 | A | 1/1906 | Carence |
| 878,223 | A | 2/1908 | Meisselbach |
| 888,869 | A | 5/1908 | Clark |

(Continued)

FOREIGN PATENT DOCUMENTS

| | | |
|---|---|---|
| DE | 199 03 782 C1 | 7/2000 |
| DE | 10 2005 037 843 A1 | 2/2007 |

(Continued)

OTHER PUBLICATIONS

U.S. Appl. No. 15/332,197, filed Oct. 24, 2016, Nasal Congestion and Obstruction Relief and Breathing Assist Devices.

(Continued)

*Primary Examiner* — Amy R Weisberg
(74) *Attorney, Agent, or Firm* — Nutter McClennen & Fish LLP

(57) ABSTRACT

Devices for nasal insertion may include an open-ended tubular element which extends along a central tube axis between a first end and a second end, the first end being larger than the second end, and in which the tubular element includes at least one spiral strut extending from the first end to the second end, and/or a nodule having an internal face, a rounded external face, and a stalk extending from the internal face and terminating in an anchor sufficiently larger than a receptacle in the tubular element and sufficiently deformable as to be pressed through the receptacle to affix the nodule to the tubular element.

5 Claims, 2 Drawing Sheets

(56) References Cited

U.S. PATENT DOCUMENTS

| | | | |
|---|---|---|---|
| 1,034,123 A | 7/1912 | Knowlson | |
| 1,077,574 A | 11/1913 | Woodward | |
| 1,087,186 A | 2/1914 | Scholfield | |
| 1,139,357 A | 5/1915 | Garske | |
| 1,160,797 A | 11/1915 | Wallin | |
| 1,256,188 A | 2/1918 | Wilson | |
| 1,311,461 A | 7/1919 | Reynard | |
| 1,322,375 A | 11/1919 | Un | |
| 1,481,581 A | 1/1924 | Woodward | |
| 1,839,606 A | 1/1932 | Simmons | |
| 2,010,485 A | 8/1935 | Heath | |
| 2,151,227 A | 3/1939 | Pawelek | |
| 2,237,954 A | 4/1941 | Wilson | |
| 2,264,153 A | 11/1941 | Bowe | |
| 2,277,390 A | 3/1942 | Crespo | |
| 2,335,936 A | 12/1943 | Hanlon | |
| 2,433,565 A | 12/1947 | Korman | |
| 2,515,756 A | 7/1950 | Bove | |
| 2,569,743 A | 10/1951 | Garlock | |
| 2,663,297 A | 12/1953 | Turnberg | |
| 2,672,138 A | 3/1954 | Carlock | |
| 3,424,152 A | 1/1969 | Kuhlman | |
| 3,463,149 A | 8/1969 | Albu | |
| 3,710,799 A | 1/1973 | Caballero | |
| 3,742,943 A | 7/1973 | Malmin | |
| 3,747,597 A | 7/1973 | Olivera | |
| 3,802,426 A | 4/1974 | Sakamoto | |
| 4,105,035 A | 8/1978 | Rella | |
| 4,120,299 A | 10/1978 | Russo | |
| 4,221,217 A | 9/1980 | Amezcua | |
| 4,267,831 A | 5/1981 | Aguilar | |
| 4,414,977 A * | 11/1983 | Rezakhany | A61F 5/08 606/199 |
| D279,708 S | 7/1985 | Child | |
| 4,573,461 A | 3/1986 | Lake | |
| 4,592,357 A | 6/1986 | Ersek | |
| 5,417,205 A | 5/1995 | Wang | |
| 5,425,359 A | 6/1995 | Liou | |
| 5,479,944 A | 1/1996 | Petruson | |
| 5,533,503 A | 7/1996 | Doubek et al. | |
| 5,601,594 A | 2/1997 | Best | |
| 5,603,317 A | 2/1997 | Farmer | |
| 5,665,104 A | 9/1997 | Lee | |
| 5,725,547 A | 3/1998 | Chuter | |
| 5,775,335 A | 7/1998 | Seal | |
| 5,816,241 A | 10/1998 | Cook | |
| 5,853,422 A | 12/1998 | Huebsch et al. | |
| 5,895,409 A * | 4/1999 | Mehdizadeh | A61F 5/08 606/199 |
| 5,925,060 A | 7/1999 | Forber | |
| 5,931,852 A | 8/1999 | Brennan | |
| 5,941,244 A | 8/1999 | Yamazaki et al. | |
| 6,004,342 A | 12/1999 | Filis | |
| 6,017,315 A | 1/2000 | Starr et al. | |
| 6,024,756 A | 2/2000 | Huebsch et al. | |
| 6,106,541 A | 8/2000 | Hurbis | |
| 6,386,197 B1 | 5/2002 | Miller | |
| 6,416,540 B1 | 7/2002 | Mathur | |
| 6,561,188 B1 | 5/2003 | Ellis | |
| 6,562,057 B2 | 5/2003 | Santin | |
| 6,602,282 B1 | 8/2003 | Yan | |
| 6,863,066 B2 | 3/2005 | Ogle | |
| 6,893,450 B2 | 5/2005 | Foster | |
| 6,978,781 B1 | 12/2005 | Jordan | |
| 7,331,989 B2 | 2/2008 | Houston et al. | |
| 7,390,331 B2 | 6/2008 | Santin et al. | |
| 7,506,649 B2 | 3/2009 | Doshi et al. | |
| 7,582,111 B2 | 9/2009 | Krolik et al. | |
| 7,637,939 B2 | 12/2009 | Tischler | |
| 7,856,979 B2 | 12/2010 | Doshi et al. | |
| 8,061,357 B2 | 11/2011 | Pierce et al. | |
| 8,262,688 B2 | 9/2012 | Santin et al. | |
| 8,403,954 B2 | 3/2013 | Santin et al. | |
| 9,199,053 B1 | 12/2015 | Allurn et al. | |
| 9,205,215 B2 | 12/2015 | McAuley et al. | |
| 9,242,080 B2 | 1/2016 | MacDonald | |
| 9,474,642 B2 | 10/2016 | Santin et al. | |
| 9,504,599 B2 | 11/2016 | Santin et al. | |
| 2003/0079749 A1 | 5/2003 | Strickland et al. | |
| 2003/0106555 A1* | 6/2003 | Tovey | A61M 15/08 128/205.27 |
| 2003/0195552 A1 | 10/2003 | Santin | |
| 2004/0015092 A1* | 1/2004 | Pettersson | A61B 5/0873 600/532 |
| 2004/0059368 A1* | 3/2004 | Maryanka | A61B 17/24 606/191 |
| 2004/0147954 A1 | 7/2004 | Wood | |
| 2005/0021073 A1 | 1/2005 | Santin et al. | |
| 2006/0085027 A1 | 4/2006 | Santin et al. | |
| 2006/0150978 A1 | 7/2006 | Doshi et al. | |
| 2006/0259064 A1 | 11/2006 | Maryanka | |
| 2006/0272640 A1* | 12/2006 | Abullon | A61F 5/08 128/203.22 |
| 2007/0010851 A1 | 1/2007 | Chanduszko et al. | |
| 2007/0066198 A1 | 3/2007 | Rambosek et al. | |
| 2007/0088334 A1 | 4/2007 | Hillis et al. | |
| 2007/0106328 A1 | 5/2007 | Wardle et al. | |
| 2007/0193233 A1* | 8/2007 | Chen | A61F 5/08 55/385.1 |
| 2007/0208368 A1 | 9/2007 | Katoh et al. | |
| 2007/0239199 A1 | 10/2007 | Jayaraman | |
| 2008/0183299 A1 | 7/2008 | Monga et al. | |
| 2008/0262531 A1 | 10/2008 | Santin et al. | |
| 2009/0093840 A1 | 4/2009 | MacDonald | |
| 2009/0095303 A1 | 4/2009 | Sher et al. | |
| 2010/0063532 A1 | 3/2010 | Moore | |
| 2011/0290256 A1 | 12/2011 | Sather et al. | |
| 2012/0283769 A1 | 11/2012 | Cruise et al. | |
| 2013/0109987 A1 | 5/2013 | Kunis et al. | |
| 2013/0131716 A1 | 5/2013 | Cruise et al. | |
| 2013/0296809 A1 | 11/2013 | Santin et al. | |
| 2014/0246023 A1* | 9/2014 | Maryanka | A61F 5/08 128/203.22 |
| 2014/0275857 A1 | 9/2014 | Toth et al. | |
| 2017/0071777 A1 | 3/2017 | Santin et al. | |
| 2017/0100275 A1 | 4/2017 | Santin et al. | |
| 2017/0273626 A1 | 9/2017 | MacDonald | |

FOREIGN PATENT DOCUMENTS

| | | |
|---|---|---|
| GB | 0 210 982 A | 2/1924 |
| GB | 2 126 101 A | 3/1984 |
| JP | 11-192251 A | 7/1999 |
| JP | 2002-301152 A | 10/2002 |
| WO | 2004/026391 A1 | 4/2004 |
| WO | 2004/069110 A1 | 8/2004 |
| WO | 2007/018458 A1 | 2/2007 |

OTHER PUBLICATIONS

U.S. Appl. No. 15/361,647, filed Nov. 28, 2016, Nasal Congestion, Obstruction Relief, and Drug Delivery.

Egan, K. et al., "A Novel Intranasal Stent for Functional Rhinoplasty and Nostril Stenosis," Laryngoscope 115 (5):903-09 (May 2005).

European Search Report and Supplementary Search Report, for EP06840036.5, dated Oct. 27, 2009 and Nov. 4, 2009.

Extended European Search Report for Application No. 08835440.2 dated Jun. 26, 2013 (6 Pages).

International Search Report, for PCT/US04/014501, dated Nov. 23, 2004.

International Search Report, for PCT/US06/61280, dated Jul. 17, 2008.

International Search Report, for PCT/US08/078781, dated Mar. 16, 2009.

Japanese Office Action dated Mar. 5, 2013 for Application 2010-528169 (3 Pages).

Japanese Office Action dated Apr. 19, 2016 for Application 2010-528169, Appeal No. 2015-000864 (11 pages).

Indian Office Action for Application No. 3358/CHENP/2008, dated Aug. 26, 2016 (7 pages).

(56) References Cited

OTHER PUBLICATIONS

International Search Report and Written Opinion for PCT/US2017/023708, dated Jun. 9, 2017 (14 pages).

* cited by examiner

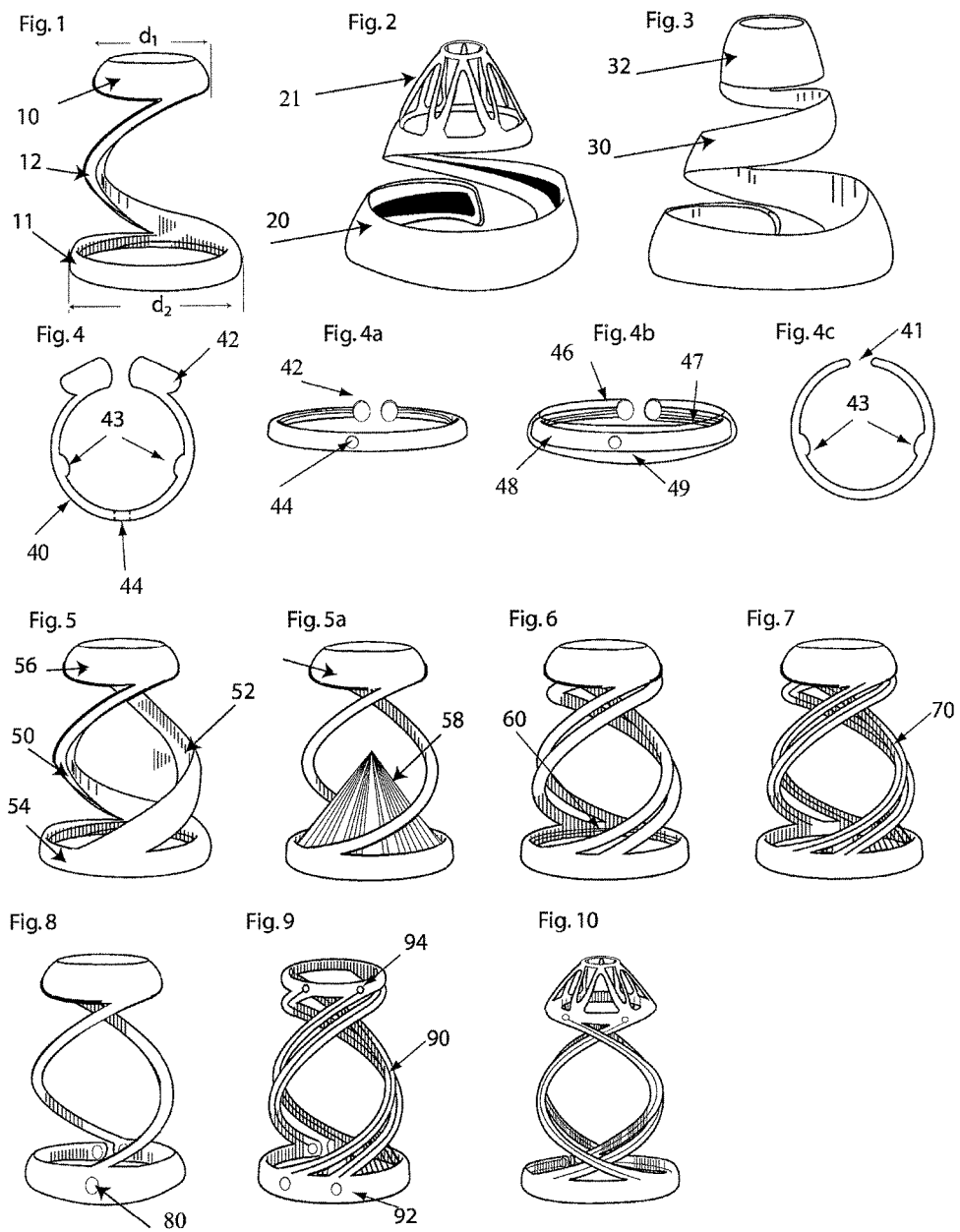

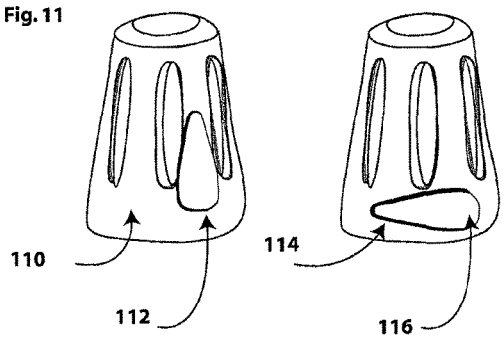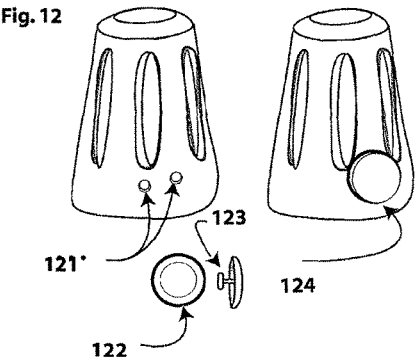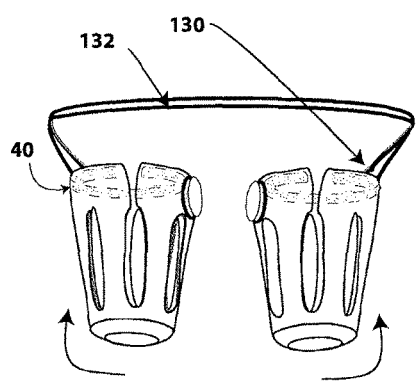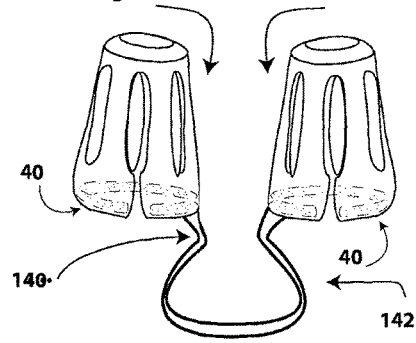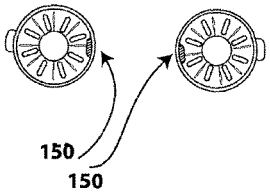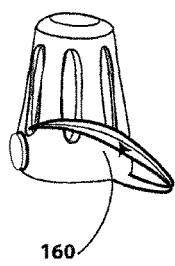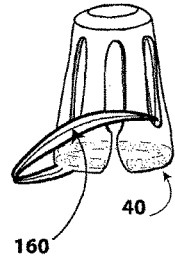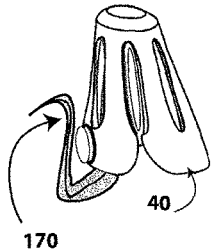

NASAL INSERTS

CROSS-REFERENCE TO RELATED APPLICATIONS

This application is a continuation of U.S. application Ser. No. 12/245,430, filed Oct. 3, 2008, entitled "NASAL INSERTS," which claims the benefit of U.S. provisional application Ser. No. 60/977,209, filed Oct. 3, 2007, both applications of which are hereby incorporated herein by reference. This application also incorporates by reference U.S. patent application Ser. No. 11/290,047, filed Nov. 30, 2005, U.S. patent application Ser. No. 10/842,220, filed May 10, 2004, U.S. patent application Ser. No. 10/434,669, filed May 9, 2003, now U.S. Pat. No. 7,390,331, and U.S. patent application Ser. No. 09/862,966, filed May 22, 2001, now U.S. Pat. No. 6,562,057.

BACKGROUND

Nasal obstruction is characterized by inflammation and/or anatomical conditions including nasal valve collapse, nasal valve obstruction, septal deviation, and medium turbinate hypertrophy. These conditions obstruct and restrict nasal airflow causing difficulties in breathing through the nose.

SUMMARY

The disclosed devices and methods may be used to increase airflow through the nasal passages. Such increase can help reduce or eliminate a wide variety of nasal, sinus, and upper airway disorders, including snoring, sleep apnea, nasal congestion, and nasal obstruction. The disclosed devices and methods may also be used to treat chronic sinusitis, rhinitis, nasal allergies, and common cold nasal congestion.

The subject matter described herein includes the following embodiments, among others:

1. A device for nasal insertion including an open-ended tubular element; wherein the tubular element extends along a central tube axis between a first end and a second end, the first end being larger than the second end; and wherein the tubular element includes at least one spiral strut extending from the first end to the second end.

2. The device of embodiment 1, wherein the spiral strut includes a stiffening element.

3. The device of embodiment 2, wherein the stiffening element is embedded in the spiral strut.

4. The device of any preceding embodiment, wherein the spiral strut has a conic helix shape.

5. The device of any preceding embodiment, wherein the first end of the tubular element includes a stiffening element.

6. The device of embodiment 5, wherein the stiffening element is embedded in the first end of the tubular element.

7. The device of any preceding embodiment, wherein the first end of the tubular element is formed by an interrupted ring.

8. The device of embodiment 7, further including a stiffening element embedded in the interrupted ring.

9. The device of embodiment 8, wherein the stiffening element is formed of a first material different from a second material forming that in which the stiffening element is embedded.

10. The device of embodiment 7, 8, or 9, wherein the ring includes at least one protuberance.

11. The device of embodiment 7, 8, 9, or 10, further including a stiffening element partially embedded in the interrupted ring so that an inner face of the stiffening element is exposed.

12. The device of embodiment 11, wherein the inner face of the stiffening element defines at least one groove.

13. The device of any preceding embodiment, wherein the tubular element defines a receptacle, and the device further includes a nodule having an internal face, a rounded external face, and a stalk extending from the internal face and terminating in an anchor sufficiently larger than the receptacle and sufficiently deformable as to be pressed through the receptacle to affix the nodule to the tubular element.

14. The device of any preceding embodiment, further including a tabular member extending from the first end and being sized and shaped to capture a nasal alar.

15. A device for nasal insertion including a first open-ended tubular element, a second open-ended tubular element smaller than the first open-ended tubular element and coaxially arranged with the first open-ended tubular element along a central tube axis, and a spiral strut affixing the first open-ended tubular element to the second open-ended tubular element.

16. A device for nasal insertion including an open-ended tubular element (a) extending along a central tube axis between a first end and a second end, the first end being larger than the second end, and (b) defining a receptacle, and a nodule including an internal face, a rounded external face, and a stalk extending from the internal face and terminating in an anchor sufficiently larger than the receptacle and sufficiently deformable as to be pressed through the receptacle to affix the nodule to the tubular element.

BRIEF DESCRIPTION OF THE DRAWINGS

FIGS. 1, 2, and 3 depict various exemplary embodiments of nasal inserts having spiral and/or helical support members.

FIGS. 4, 4A, 4B, and 4C depict exemplary embodiments of the construction of the constituent part of a nasal insert that may serve as a stiffening ring or hoop, which is embedded or over molded. This embodiment may be fashioned separately or be integrated into the nasal insert.

FIGS. 5, 5A, and 6-10 depict various exemplary embodiments of nasal inserts having helical support members.

FIGS. 11-16, 16A, 17, and 18 depict various exemplary embodiments of nasal inserts having protuberances.

DETAILED DESCRIPTION

FIG. 1 illustrates an embodiment of a nasal insert that includes upwardly spiraling support member or strut 12 extending between top ring 10 and bottom ring 11. The top ring may have a diameter $d_1$ or other transverse measure that is smaller than a diameter $d_2$ or other transverse measure of the bottom ring. FIGS. 2, 3, 5, 5A, and 6-10 show various other embodiments of nasal inserts with spirally- or helically-oriented support member(s).

The various constituent parts of a nasal insert may be made from different materials and/or have different stiffnesses. Nasal insert constituent parts may be formed from a first material that is partially or completely encapsulated in or coated by a second material. While it may be preferable that the surfaces of the insert that contact nasal surfaces are made of soft plastics or polymers, inserts may also be made of metals, plastics, and/or polymers.

For example, a nasal insert may have constituent part(s) made from a relatively stiff material coated with a relatively soft and/or pliable material. In some embodiments, constituent part(s) of an insert may be made from one or more pliable or flexible materials, that range in Instantaneous Hardness, as rated by ASTM D-2240, from Shore 00 to Shore D 90. Certain portions of constituent part(s) of an insert may be made from one material durometer, while others may be made from two. For example, the bottom ring may be stiffened with the addition of an inner hoop or stiffening ring of a first Instantaneous Hardness ASTM D-2240 value material that is over molded or embedded in a second different Instantaneous Hardness ASTM D-2240 value material, while the rest of the insert is made from either the same Instantaneous Hardness ASTM D-2240 value material as the second material, or from a third Instantaneous Hardness ASTM D-2240 value material different from the first and second materials.

In some embodiments, the materials may be bio-absorbable and/or biodegradable materials. The insert may be placed in the nose to aid correct structural growth or during or following surgery to stent the airway open to aid healing. Placed in such a way, an insert made of bio-absorbable or biodegradable materials will absorb and/or disappear over time eliminating the need to surgically remove it.

If two or more flexible materials are used to form a constituent part of a nasal insert, they may be bonded chemically, mechanically, or chemically and mechanically to one another. Similarly, if different constituent parts of a nasal insert are made from different materials (or different combinations of materials, such as when two constituent parts have certain material(s) in common and certain material(s) not in common) they may be bonded, chemically, mechanically or chemically and mechanically to one another.

The support member 12 may be made from a material that is selected for its elastic properties so that support member 12 may serve as a spring mechanism between one or more tubular elements, 10 and 11. The support member may contain a stiffening element embedded or over molded inside to provide vertical support. This member may be made with two distinct materials. The tubular elements may be made from a third, distinct, material.

FIG. 2 illustrates a second embodiment where the spiral support member 20, which may contain a stiffening element to provide vertical support, serves as a spring mechanism for one tubular element 21, which has openings through the wall, and may be made with the first material, or with a second, distinct, material. The spiral support member, as with other constituent parts, may be embedded inside or overmolded with a less stiff material.

FIG. 3 illustrates a third embodiment where the spiral support member 30 made of a first material, serves as a spring mechanism for one tubular element 32 that may be made with the first material, or with a second, distinct, material.

FIG. 5 illustrates an insert having two tubular elements 54 and 56, supported by two spiral support members 50 and 52. The insert may also include a filter, such as conical filter 58, shown in FIG. 5a. The filter may be affixed to the insert in a variety of ways, such as by snap-fitting, press-fitting, interference fit, integral formation, etc. The insert and filter may define groove(s) and complementary ridge(s).

The spiral support members may wrap in the same direction and may be placed opposed to one another in connecting to the first tubular element, such as shown in FIG. 5.

The first material may be an inner ring which may have an interruption as illustrated in FIG. 4 (top view) 40 and FIG. 4a (side view), that may have two or more protrusions 42 (outward-facing), 43 (inward-facing), and/or one or more holes 44 through the ring. FIG. 4b illustrates an embodiment of an inner ring 48 embedded in an outer material 49, in a manner such that the inner facing surface of the inner ring is exposed 46. This inner surface can define one or more grooves 47.

FIG. 8 illustrates an example of a FIG. 4 inner ring integrated into a nasal insert, in which the protrusions on the inner ring are mechanically and chemically bonded to the second material, and appear on the outer surface at anchor holes 80.

The first material (i.e., the stiff core) may also be a vertically oriented support member that may wrap upwards in a circular direction to form a series of curves or one or more helixes (element 60 in FIG. 6; element 70 in FIG. 7). FIG. 9 shows cores 90 embedded in helical support members with anchor holes or protrusions at the start 92, end 94, or mid points as necessary.

The first material may have ring, spiral, horizontal or vertical parts that are formed as one part or are formed as separate parts and then assembled, as demonstrated in FIG. 10.

Definitions

Pliable—capable of being bent or flexed or twisted without breaking

Flexible—Capable of being bent or flexed, repeatedly without injury or damage.

Resilient—Capable of returning to an original shape or position, as after having been compressed.

Spiral—(a) A curve on a plane that winds around a fixed center point at a continuously increasing or decreasing distance from the point; (b) A three-dimensional curve that turns around an axis at a constant or continuously varying distance while moving parallel to the axis; a helix, such as a cylindrical or conic helix.

Helix—A three-dimensional curve that lies on a cylinder or cone, so that its angle to a plane perpendicular to the axis is constant.

FIGS. 11-17 depict exemplary embodiments of nasal inserts having non-ridge-containing protrusion(s). Including a protrusion on an insert may aid in reshaping the nasal air space, through gentle outwardly facing pressure by the insert on the nasal pathway, to allow greater airflow to be inhaled through the nasal pathway. The protrusions (nodules) may be located on any surface of the nasal insert. The one or more protrusions may be custom-positioned on the insert to facilitate a refined and personal fit.

As shown in FIGS. 11-13 and 16-17, a nasal insert may include one or more nodules (rounded, non-ridge containing protuberances) 112 (FIG. 11) and 124 (FIG. 12). A nodule or protuberance may be shaped like half of a pear that is cut in the longitudinal or latitudinal plane, or as a button, a rounded plane, as a semisphere or hemisphere, or as other rounded shapes. Nodules may be convex as shown, or concave, or both, as desired to conform to or interface with nasal mucosa.

Nodules may be integrally formed in a nasal insert or may be formed as a separate part and assembled (FIG. 12). The nodule may be formed from a material having a different durometer than that of the nasal insert. The nodule may be softer than the material of the nasal insert. The nodule may include or contain a magnet. Such a magnet may be sized, shaped, positioned, and/or provided with sufficient magnetic strength so that it may attract a second magnet included in or contained in the nodule of a second nasal insert, or included in or contained in an exterior tabular element. The nodule(s) may be integrated or formed separately in a varying array of nodule shapes 112, 122 and may protrude at varying slopes so as to allow for maximum customization. Nodules formed separately may be made part of a nasal insert kit for an individual's selection. The nodules may attach with a self-securing mechanism 123, which may be fitted through one or more through-wall openings or receptacles 121. Customization and comfort may be enhanced and this permits a more affordable method to customize the nasal insert for improved function and comfort.

The nasal insert with the nodules may be formed so that they are connected by a member that originates from the inner surface wall, as shown in cross section FIG. 15, 150 of the tubular element, and extends distal from the tubular element FIG. 13, 130 and then through a rounded or angular corner 132 continues across a width at least double the span of the tubular elements diameter 134 where a mirrored rounded or angular corner 136 then returns the connecting member to the second tubular element on the inner surface wall.

In use, the tubular elements may be rotated 180 degrees upward, so that the connecting member 140 turns around and forms a loop 142. The ends 150 of the connecting member may originate inside the tubular element as demonstrated in FIG. 15 in a profile drawing.

FIGS. 16, 16A, 17, and 18 show another embodiment, in which the tubular elements may include a tabular member 160, 170 that is designed in the shape of an arc. The tabular member may be so sized and shaped as to capture the nasal alar 180, thereby helping to secure the tubular member in the nose.

The features described herein may be combined with the various features described in U.S. patent application Ser. No. 11/290,047, filed Nov. 30, 2005, U.S. patent application Ser. No. 10/842,220, filed May 10, 2004, U.S. patent application Ser. No. 10/434,669, filed May 9, 2003, and U.S. patent application Ser. No. 09/862,966, filed May 22, 2001, now U.S. Pat. No. 6,562,057, which are incorporated by reference herein for such teachings. For example, the nasal inserts described herein may include tabs, connecting members, filters, intranasal drug coating/delivery, interrupted members, shapes, and other features as described in the cited references.

I claim:

1. A device for nasal insertion comprising:
   an open-ended tubular element (a) extending along a central tube axis between a first end and a second end, the first end being larger than the second end, and (b) defining a receptacle formed through a sidewall of the tubular element between the first end and the second end; and
   a nodule comprising an internal face, a rounded external face, and a stalk extending from the internal face and terminating in an anchor sufficiently larger than the receptacle and sufficiently deformable as to be pressed through the receptacle to affix the nodule to the tubular element.

2. The device of claim 1, further comprising a plurality of nodules, each nodule having round external face and configured for affixing to the receptacle.

3. The device of claim 2, wherein the nodules have varying shapes.

4. The device of claim 2, wherein the device defines a plurality of nodule receiving receptacles.

5. The device of claim 1, wherein the device defines a plurality of nodule receiving receptacles.

* * * * *